United States Patent [19]

Kaplan et al.

[11] Patent Number: 5,006,154

[45] Date of Patent: Apr. 9, 1991

[54] METHOD OF SYNCHRONIZING FLOWERING IN PLANTS

[75] Inventors: Stuart L. Kaplan; John R. Goss, both of Modesto, Calif.

[73] Assignee: Shell Oil Company, Houston, Tex.

[21] Appl. No.: 889,532

[22] Filed: Jul. 24, 1986

[51] Int. Cl.$^5$ .................. A01N 43/60; A01N 43/08
[52] U.S. Cl. ........................................ 71/92; 71/65; 71/76; 71/89
[58] Field of Search ........................... 71/92, 89, 76

[56] References Cited

U.S. PATENT DOCUMENTS

| | | | |
|---|---|---|---|
| 4,038,065 | 7/1977 | Johnson et al. | 71/76 |
| 4,069,614 | 1/1978 | Hicks et al. | 47/58 |
| 4,359,576 | 11/1982 | Ten Haken et al. | 71/92 |
| 4,729,783 | 3/1988 | Regel et al. | 71/92 |
| 4,747,869 | 5/1988 | Krämer et al. | 71/92 |

*Primary Examiner*—Glennon H. Hollrah
*Assistant Examiner*—S. Mark Clardy

[57] ABSTRACT

A method for synchronizing the flowering of two genotypes of a species of a plant, which genotypes do not naturally flower at the same time after emergence from the soil, that method comprising providing in the soil in which the genotype that naturally flowers earlier is growing, or is to be grown, a dosage of a defined genus of compounds sufficient to delay the time of flowering of that genotype so as to synchronize its flowering with the flowering of the later-flowering genotype.

27 Claims, No Drawings

METHOD OF SYNCHRONIZING FLOWERING IN PLANTS

BACKGROUND OF THE INVENTION

To effect cross-pollination between genotypes of plants of the same species, viable pollen grains from the candidate male parent plant must contact stigmata of the candidate female parent at a time when the stigmata are receptive. In plants generally, the stigmata become receptive at approximately the same time the pollen is shed—i.e., at flowering. Not all genotypes of a species of a plant flower at the same length of time after emergence from the soil, so that in cases where the genotypes under consideration as candidate parents for cross-pollination would not naturally flower at the same time, it is necessary to synchronize the flowering to enable cross-pollination. Such may be accomplished by planting the later-flowering prospective parent sufficiently earlier that it flowers at the same time as the earlier-flowering parent, or vice versa. However, such staggered planting is not always sufficiently effective: with respect to some grass crop plants, such as wheat, the seed may be planted in the Fall of the preceding year, with growth resuming the following Spring. Since both candidate parents would resume active growth at approximately the same time, and since both would be vernalized and into the reproductive stage of growth, staggering planting dates has only a small effect on when flowering occurs. Therefore, altering the pollination date by one day may require altering the planting date by ten days. Since it may be necessary to alter the pollination date by several days—i.e., three to twenty-one days, or more—in order to produce certain hybrids, alteration of the planting date as a means of altering the pollination date is impractical on a large scale. Thus, hybridizers do not always have an opportunity for controlling the synchrony of flowering by adjusting planting dates. It is, therefore, desirable that there be some method for synchronizing flowering of plants that is not dependent upon the time of planting.

DESCRIPTION OF THE INVENTION

It now has been found that the time of flowering of a plant is delayed, without adverse effect upon the capability of the plant to form pollen and seed, by providing in the soil in which the plant is growing, or is to be grown, a chemical that is absorbed into the vascular system of the plant from its soil rhizosphere via the underground parts of the plant, and inhibits biosynthesis of gibberellic acid(s) in the plant by inhibiting oxidation of kaurene to kaurenoic acid, one of the steps that occurs in the biosynthesis of gibberellic acid(s). All such chemicals are characterized by the fact that they cause reduction in longitudinal cell growth in plants, and thus are commonly designated as "dwarfing agents".

It has been found that the effect is passed from the treated plant to its progeny—i.e., flowering is delayed in the plants which grow from the seed of the treated parent plants.

The finding that such chemicals delay the time of flowering of plants and their progeny provides the invention, which is a method for synchronizing the flowering of two genotypes of a species of a plant which genotypes do not naturally flower at the same time after emergence from the soil.

The degree of synchronization of flowering between two plant genotypes is known as the "nick". The chemicals contemplated in this invention thus may be termed "nick-facilitating agents", and for brevity hereinafter will be referred to as "nick agents".

The method is particularly of interest when the two genotypes are species of a plant that are to be used in cross-breeding. The method comprises providing in the soil in which the genotype that naturally flowers earlier is growing, up to the stage of its development just prior to when anthesis begins, or is to be grown, a dosage of a nick agent as defined above sufficient to delay the time of flowering of that genotype to synchronize its flowering with the flowering of the later-flowering genotype. In another aspect, the invention provides a method for producing hybrid seed from two genotypes of a species of plant, which genotypes do not naturally flower at the same time after emergence from the soil, that method comprising providing in the soil in which the earlier-flowering candidate parent genotype is growing, up to the stage of its development just prior to when anthesis begins, or to be grown, a dosage of a nick agent as defined above sufficient to cause that genotype or its progeny to flower at approximately the same time as the later-flowering candidate parent genotype flowers, thereafter causing cross-pollination between the two candidates, allowing the female candidate to develop until the seed is mature and harvesting the seed. In the case where the species of plant is monoecious, and can self-pollinate, interference in the production of the desired hybrid seed by the self-pollination effect can be avoided by employing a male-sterile plant as the candidate female parent. Male sterility can be effected in several ways—e.g. genetically, mechanically or chemically.

In yet another aspect, the invention provides a method for producing parental seed of a genetic or cytoplasmic male-sterile genotype, commonly referred to in the industry as "A-line" that is used in the production of hybrid seed. A-line plants are the female parent in hybrid seed production because they produce little or no viable, functional pollen. A-line seed is produced by the fertilization of A-line plants by plants that are genetically nearly identical to the A-line except for their ability to produce viable, functional pollen. This latter genotype is commonly referred to in the industry as "B-line", the "B-line maintainer", or the "maintainer". However, A-lines and corresponding B-lines, although genetically quite similar, do not necessarily flower synchronously. The invention herein described could therefore be used to delay flowering of the earlier flowering genotype for the purpose of producing more A-line seed.

In terms of chemical structure, a variety of chemicals that are effective as nick agents in the method of the invention are known in the prior art. One such class is that disclosed in U.S. Pat. No. 4,359,576, namely compounds of the formula

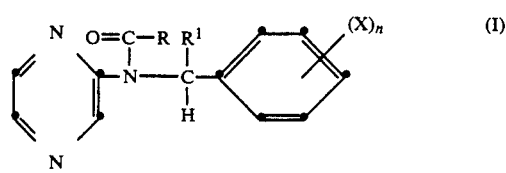

(I)

wherein the symbols have respective meanings defined in the patent. Of particular interest is the individual species wherein R is tertiary-butyl, $R^1$ is hydrogen and $(X)_n$ is 4-chloro.

Other contemplated chemicals are disclosed in the following patents:

(A) U.K. patent 1,218,623, being compounds of the formula

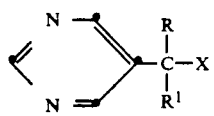

wherein the symbols have respective meanings defined in the patent. Of particular interest are the individual species of this class wherein (a) X=hydroxyl, R=isopropyl and $R^1$=4-(trifluoromethoxy)phenyl, this species being commonly known as flurprimidol, and (b) X=hydroxyl, R =cyclopropyl and $R^1$ =4-(methoxy)phenyl, this species being commonly known as ancymidol.

(B) U.K. patent 1,361,816, being compounds of the formula

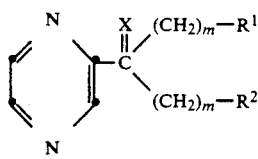

wherein the symbols have respective meanings defined in the patent.

(C) U.S. Pat. No. 4,243,405, being compounds of the formula

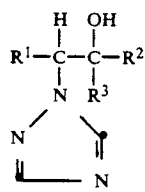

wherein the symbols have respective meanings defined in the patent. Of particular interest is the individual species of this class wherein (a) $R^1$=4-chlorobenzyl, $R^2$=H and $R^3$=tertiary-butyl, this species being commonly known as paclobutrazol, and (b) $R^1$=2,4-dichlorobenzyl, $R^2$=H and $R^3$=tertiary-butyl, this species being commonly known as dicnlorobutrazol. Enantiomeric forms of these chemicals are the subject of British Patent Application 2,041,927

(D) U.S. Pat. No. 4,315,764, being compounds of the formula

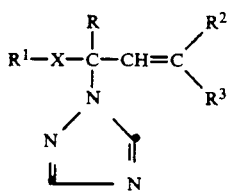

wherein the symbols have respective meanings defined in the patent.

(E) U.K. patent application 2,046,260, being compounds of the formula

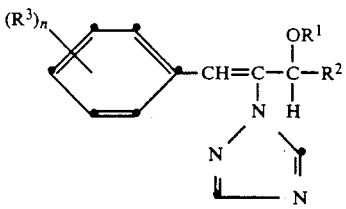

wherein the symbols have respective meanings set out in the specification. Of particular interest are the species wherein (a) $(R^3)n$=2,4-dichloro, $R^1$=hydrogen, and $R^2$=tert-butyl, and (b) $(R^3)n$=4-Cl, $R^1$=hydrogen and $R^3$=tert-butyl.

(F) Other chemicals of similar classes disclosed in Japanese Patent 85263174, European Patent Application 54431, German Offenlegungschrift 3,045,182, U.K. Patent Application 2,041,927, U.S. Pat. No. 4,452,625, German Offenlegungschrift 2,737,489, U.K. Patent Application 2,081,700, European Patent Application 25516, U.K. Patent Application 2,050,334, U.S. Pat. No. 4,554,285, U.S. Pat. No. 4,554,007, and U.S. Pat. No. 4,551,469.

(G) European Patent Application 62236, 44407 and 43923, being compounds of the formula

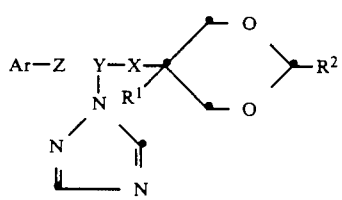

wherein the symbols have respective meanings set out in the patent specifications, particularly the members of this subclass of the formulae

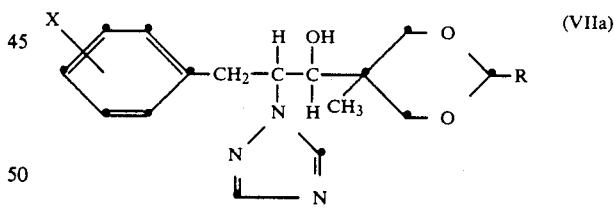

and

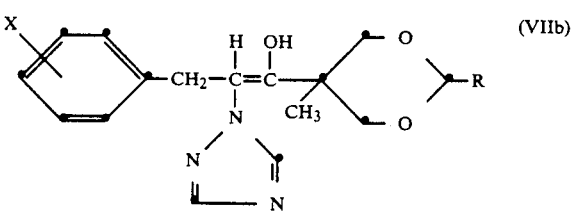

wherein X is 4-alkyl, trifluoromethyl or halogen and R is hydrogen or alkyl, the individual species of formula VIb wherein X=4-trifluoromethyl and R=hydrogen being most of interest.

(H) German Offenlegungschrifts DE 3,144,670 and DE 3,329,128, being compounds of the formulae

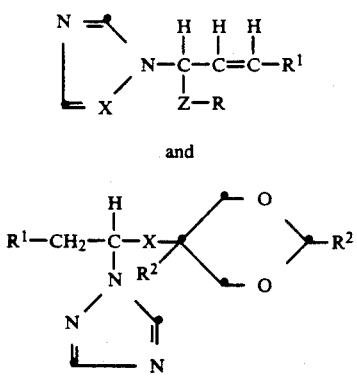

(VIIIa)

and

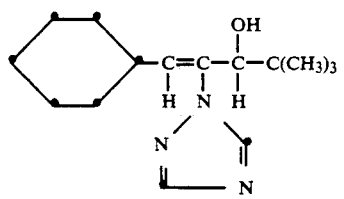

(VIIIb)

wherein the symbols have respective meanings set out in the respective specifications, particularly the compound of German Offenlegungschrifts DE 3,302,120 and -122: (E)-1-cyclohexyl-4,4-dimethyl-3l-hydroxy-2-(1,2,4-triazolyl)-1-pentene, of the formula

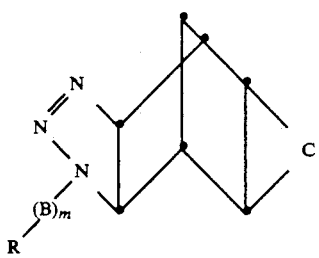

(VIIIc)

(I) A structurally different class of suitable chemicals is disclosed in U.S. Pat. No. 4,189,434, being compounds of the formula (IX)

wherein the symbols have respective meanings defined in the patent, particularly the individual species wherein m=zero, R=4chlorophenyl and C=—N=N—, commonly known as tetcyclasis.

Suitably, the nick agent is introduced into the soil in which the seed of the earlier-flowering genotype is to be sown, or in which the genotype is growing, up to the stage of its development just prior to when anthesis begins.

The effect of the nick agent upon the flowering of the plant and its progeny is directly related to the dosage of the agent that is applied—the higher the dosage, the greater the delay in flowering. A dosage as low as 0.1 part by weight of the agent per million parts by weight of the dry soil (i.e., ppm) surrounding the treated plant is known to significantly delay flowering. These nick agents are not known to be phytotoxic at higher dosages, so that higher dosages—up to, for example, 8 ppm on the same basis—may be used to delay flowering for a longer time. Expressed in terms of conventional practice, such dosages are attained by applying to the soil a formulation which provides from about 0.1 kilogram to about 8 kilograms of the nick agent per hectare of treated soil. The effective dosage of the nick agent also is related to the stage of development of the plant to be treated, a lower dosage applied earlier in the development of the plant having the effect of a higher dosage applied later in the development of the plant. To minimize the amount of the compound of the agent that will be required, and to avoid application of the compound to the soil as a separate operation, it thus may be desirable to apply the agent at the time the seed of the plant is sown. However, because the accuracy with which the degree of synchrony can be estimated increases as the involved plant develops, it may be found desirable to apply the nick agent at a later stage in the development of the plant. Although these nick agents delay flowering in the progeny of treated plants, the effect is less pronounced than the delay produced in the treated parent plants, and this factor must be taken into account when selecting a dosage of the agent to produce a given delay in flowering in the progeny. In any particular case, involving two particular genotypes for which the times from emergence from the soil to flowering are known, simple preliminary tests will establish the dosage and time of application of the nick agent to be used with respect to the earlier-flowering genotype to synchronize its time of flowering with that of the later-flowering genotype.

The effect of the nick agent in delaying flowering can be neutralized or even somewhat reversed (to effect earlier flowering) by applying a gibberellic acid to the foliage of the treated plant. The degree of neutralization or reversal depends upon the particular gibberellic acid (or mixture of such acids) used, the time or times of application relative to the development of the plant, the amount of the nick agent that had been used, and the response of the treated plant—all factors that can readily be resolved by one skilled in the art. In general, it will be found that the gibberellic acid will act quite rapidly. This phenomenon provides a further means for controlling the synchronization of flowering with greater precision than might be obtained by the application of the nick agent alone, since the agent could be applied at the time of planting—perhaps in deliberate excess—then the gibberellic acid applied close to the time of flowering, when the degree of synchrony of flowering could be estimated with greater accuracy. Treatment with the gibberellic acid also could be used if it becomes evident that an inadvertent excess of the nick agent had been applied. The gibberellic acid suitably is applied as a dilute solution.

The method of the invention is applicable to flowering plants, generally, being of interest with respect to the breeding and hybrid production of such crop plants as wheat, barley, oats, rye, flax, hops, maize, sorghum, buckwheat, millet, triticale, sesame, soybeans, rapeseed, sunflowers, safflower, lentils, mustard, cotton, peanuts, rice, sugarbeets, sugarcane and tobacco; vegetables such as tomatoes, beans, peas, celery and onions; grassy and broadleaved forage crops, such as alfalfa, clover, sudangrass, lespedeza, vetch, fescues, bromegrasses and orchardgrass; cucurbits such as cucumbers, squash and melons; crucifers (cole crops) such as cabbage, broccoli and cauliflower; and ornamental plants such as annual and perennial plants of interest in the nursery or home garden trades. The method of the invention also can be used in effecting wide crosses, between different species of plants, where such is possible genetically—as in cross-breeding of different species of cultivated plants, crossbreeding of different species of cultivated and wild plants, and cross-breeding of crop plants with their wild relatives. The method is of particular interest for effecting hybridization of grass crop plants, especially those commonly designated as cereal grain and feed grain plants, and forage plants. Typical grass crop plants include for example, such cereal grains as wheat and other species of the genus Triticum; barley; rye; oats; corn (maize); sorghum; pearl millet; finger millet; triticale; sugarcane; rice and buckwheat; forage crops and turf grasses, for example, *Paspalum* species such as bahiagrass, *Cynodon* species such as bermudagrasses, *Poa* species such as bluegrasses, *Bromus* species such as bromegrasses, *Dactylis glomerata* (orchardgrass), *Festuca* species such as fescues, *Agropyron* species such as wheatgrasses, and sudangrass and other species of the genus Sorghum. The method also is of particular interest for effecting hybridization of broad-leaved crop plants such as the oil-seed crops, flax, rape, cotton, sunflowers, and members of the Fabaceae family (e.g. soybeans, peas, beans, lupines and clover).

The necessary dosage of the nick agent can be provided in the plant rhizosphere by applying a suitable formulation of the agent to the soil, or by treating the seed with the agent before the seed is sown.

The formulation can be mixed with the soil by any convenient conventional means—for example, by applying the formulation (liquid or solid) to the surface of the soil, with or without mixing with the soil, with or without watering-in the formulation.

For application to the soil, the nick agent is conveniently formulated for use as granules or powders containing a solid diluent impregnated with the compound. Such formulations usually contain from about 1 to about 50% by weight of the agent. Alternatively, the nick agent can be applied as a drench—that is, as a solution or dispersion of the agent in a non-phytotoxic solvent or liquid diluent, suitably water. Such drenches can be prepared by diluting with water a concentrate containing the nick agent, an emulsifying agent, and preferably an organic solvent, such as toluene. The nick agent can be applied by broadcasting, or by band, furrow or side-dress techniques, and may be incorporated or not. More details regarding the manner in which the agent can be formulated for use in the method of the invention are set out in the cited patents and patent applications that disclose the agents.

For application of the nick agent with the seed, the seed can be soaked in a solution of the agent, or the seed can be coated with a suitable formulation of the agent. For this purpose, conventional formulations and conventional coating techniques are suitable. One technique that is suitable is that commonly known as the slurry method, wherein correctly proportioned quantities of seed and agent in the form of a suspension are brought together more or less continuously. Very little of the seed and treating agent are in the treating vessel at any one time and efficient coverage of the entire seed coat with the slurry is readily achieved. Slurry treated seed seldom requires a separate drying process. Slurry treatment of seed is commonly employed in the seed-treatment art. In another technique, the seed is coated with an adherent solid formulation of the agent blended with or impregnated onto a solid inert carrier. The carrier should not be hygroscopic so that the final formulation will remain dry and free flowing. Suitable inert carriers are those well known to the art including various grades of carbon, the clays such as the kaolinites, the bentonites and the attapulgites; other minerals in natural state such as talc, pyrophyllite, quartz, diatomaceous earth, fuller's earth chalk, rock phosphate and sulfur; and chemically modified minerals, such as acid washed bentonites, precipitated calcium phosphates, precipitated calcium carbonate and colloidal silica. These diluents may represent a substantial portion, for example, 50 to 98 percent by weight of the entire formulation.

It is essential that the seed coating formulation be brought in intimate contact with the seed. To achieve this, especially in the case of slurry and dust seed-coaters, it is frequently necessary to add such agents as methylcellulose or ethylcellulose to promote adherence. The quantity of such an adherence promoter required in the seed-coating formulation will vary from 0.1 percent by weight to about 20 percent by weight depending upon the formulation and the type of seed to be treated. The coating of the seed is effected mechanically by means of pan or disc coaters, or by fluidized bed techniques.

The efficacy of typical individual species of the nick agents of the invention in delaying the time of flowering of a typical genotype of wheat plants was demonstrated in the following experiments.

EXAMPLE 1

Wheat of the variety "TAM 101" (a hard red winter wheat) was seeded, using a grain drill, in rows 15 centimeters apart, at the rate of 35 kilograms of seed per hectare. The soil was Hanford sandy loam. The plots were watered immediately, and the seedlings emerged seven days later. The plots were arranged in a randomized completeblock design, each with five blocks. Plots were 10 rows wide (1.52 meters) and 6.58 meters long. Two untreated checks were included in each block.

The test compound was N-(tert-butylcarbonyl)-N-(4'-chlorophenylmethyl)aminopyrazine —i.e., Formula I, R = tertiary-butyl, $R^1$ = hydrogen, $(X)_n$ = 4-chlorine, hereinafter designated as Compound A.

The test compound was applied as an emulsible concentrate containing 200 grams of the compound per liter of the formulation. The test compound was applied at rates of 0.5, 1.0, 2.0 and 4.0 kilograms of the compound per hectare, by spraying the formulation onto the surface of the soil in which the plants were growing, then "watered-in" by spray irrigation. The compound was applied when three leaf collars were first visible in the main stems.

The plots were fertilized and watered according to customary practices for raising wheat crops in the area.

The effect of the test compound upon flowering of the plants was determined by selecting a reference day (March 31) when the plants were maturing but before any had produced visible heads, then noting the number of days thereafter when visible heads were produced. The results are set out in Table I.

TABLE I

| Application Rate (kg/ha) | Heading Date (days after March 31) |
|---|---|
| 0.0 | 12 (D[a]) |
| 0.5 | 16 (C) |
| 1.0 | 21 (B) |
| 2.0 | 28 (A) |
| 4.0 | 32 (A) |
| M.S.D.[b] | 4.1 |

TABLE I-continued

| Application Rate (kg/ha) | Heading Date (days after March 31) |
|---|---|
| S.D. | 2.3 |

[a] Values within a column not followed by the same letter are significantly different based on a Tukey's studentized range test (alpha = 0.05).
[b] Minimum significant differences (M.S.D.) according to Tukey's studentized range test.

It was found that the test had no significant adverse effect upon the yield of seed in any of the dosages that were applied.

EXAMPLE 2

The tests described in Example 1 were repeated, except that the soil in which the plants were grown was a Tujunga sand. The results are set out in Table II.

TABLE II

| Application Rate (kg/ha) | Heading Date (days after March 31) |
|---|---|
| 0.0 | 11 (E[a]) |
| 0.5 | 15 (D) |
| 1.0 | 21 (C) |
| 2.0 | 24 (B) |
| 4.0 | 29 (A) |
| M.S.D.[b] | 1.8 |
| S.D. | 1.0 |

[a] Values within a column not followed by the same letter are significantly different based on a Tukey's studentized range test (alpha = 0.05).
[b] Minimum significant differences (M.S.D.) according to Tukey's studentized range test.

Again, the test compound had no significant adverse effect upon the yield of seed.

EXAMPLE 3 Effect upon progeny

In California in the Fall, spring wheat plants of the variety "Yolo" growing in a field were treated at the three-leaf stage with Compound A at the rates of 0.0, 0.5, 1.0, 2.0 and 4.0 kilograms of Compound A per hectare. Seed from these treated plants were harvested. Ten seeds from plants in each of the treatment rate series were planted in an 8-inch pot, with four replicates of each of the series. The seeds were planted in a commercial potting mix, and were watered and fertilized as necessary. After planting, the pots were held in a greenhouse, at an average day/night temperature of 22/17° C., average relative humidity of 50%, and a 16/8-hour day/night photoperiod cycle. After emergence, the number of plants in each pot was reduced to seven.

The heading date of the plants in each pot was the number of days after planting when the bottoms of the inflorescences in four of the plants in the pot had emerged from the flag leaf sheath.

The effect of the treatment of the parent plants upon their progeny is summarized in Table III.

TABLE III

| Application Rate, Compound A, on Parental Generation (kg/ha) | Heading Dates of Progeny (Days After Planting) |
|---|---|
| 0.0 | 47.3 (a)* |
| 0.5 | 48.0 (ab) |
| 1.0 | 48.5 (b) |
| 2.0 | 48.6 (b) |
| 4.0 | 50.3 (c) |

*Values followed by different letters are significantly different, based upon a least significant difference (P = 0.05).

EXAMPLE 4

Soybeans of the variety "McCall" were seeded in 3-gallon pots, 5 seeds per pot, containing a potting mix consisting of a 2:1 v:v mixture of Hanford soil and perlite. After planting, the soil was treated with Compound A at rates of 0, 1, 2 and 4 kilograms of Compound A per hectare. The compound was applied by spraying a formulation consisting of a 1:1 v:v mixture of acetone and water containing 0.75% v:v Tween 20 surfactant, and sufficient Compound A to provide the needed dosage thereof. The pots then were watered lightly, arranged in a randomized complete-block design in a greenhouse, and held at an average day/night temperature of 80/66° F., and a 16/8 hour day/night photoperiod cycle. The plants were watered and fertilized as needed. The effect of the Compound A on the time of first flowering was observed and compared to the controls. The following results were obtained.

TABLE IV

| Application Rate, Compound A, Generation (kg/ha) | Delay in Opening of First Flowers (Days) |
|---|---|
| 0 | 0 |
| 1 | 9 |
| 2 | 13 |
| 4 | 14 |

EXAMPLES 5–8

In the following tests, a standardized protocol was employed: Spring wheat (variety "Yocoro rojo") was planted in 6-inch pots, 8 seeds per pot, in a medium consisting of a 1:1 v:v mixture of pasteurized Hanford sandy loam soil and perlite. The planted pots were held in the greenhouse under the conditions described in Example 3. One week after germination, all of the pots were thinned, to leave four plants per pot. The plants were treated with the test chemical when three leaf collars were first visible on the main stems. The treatments were made by drenching the soil in each pot with 100 ml of an aqueous solution of the test chemical containing 0.75% (v:v) Tween 20 surfactant, to provide the required dosage of the test chemical, of 0.2 and 2.0 kilograms/hectare. Untreated pots, and pots treated with the formulation containing no test chemical, were used as controls. At the time of the treatment, the soil in all of the pots was uniformly moist. All treatments were replicated thrice, and after treatment the pots were set up in a randomized complete block design in the greenhouse. Watering was withheld until 48 hours after treatment. The treatments were evaluated by determining the number of days from planting until emergence of the bottom of the inflorescence from the flag leaf collar in at least two of the four plants in each pot.

In all cases, the formulations containing no test chemical had no significant affects upon the heading date. The test chemicals were:

Flurprimidol = Compound B
Ancymidol = Compound C
Paclobutrazol = Compound D
Tetcyclasis = Compound E
1-(2,4-dichlorophenyl)-
2-(1,2,4-triazol-1-yl)-
4,4-dimethyl-1-pentene = Compound F
1-(4-chlorophenyl)-2-
(1,2,4-triazol-1-yl)-

-continued

| 4,4-dimethyl-1-pentene = Compound G |

TABLE V

| Application Rate (kg/ha) | Compound | Heading Date (days after planting) |
|---|---|---|
| 0.0 | | 44.3 (a)* |
| 0.2 | D | 49.7 (d) |
| | E | 46.0 (b) |
| | F | 45.7 (ab) |
| | G | 47.7 (c) |
| 2.0 | D | 53.3 (e) |
| | E | 48.7 (c) |
| | F | 47.3 (bc) |
| | G | 50.7 (d) |

*Values followed by different letters are significantly different, based on a LSD (P ≤ 0.05).

EXAMPLES 9-10

Using the test protocol described in Examples 5-8, Compounds B and C were tested, with the following results.

TABLE VI

| Application Rate (kg/ha) | Heading Date (days after planting) | |
|---|---|---|
| | Compound B | Compound C |
| 0.0 | 52.0 (a) | 51.0 (a)* |
| 0.2 | 57.0 (b) | 56.0 (b) |
| 2.0 | 62.3 (c) | 61.3 (c) |

*Values followed by different letters are significantly different, based on a LSD (P ≤ 0.05).

We claim:

1. A method for synchronizing the flowering of two genotypes of a species of a plant that is to be used in cross-breeding, which genotypes do not naturally flower at the same time after emergence from the soil, that method comprising providing in the soil in which the genotype that naturally flowers earlier is to be grown, or is growing, up to the stage of its development just prior to when anthesis begins, a chemical that is absorbed into the vascular system of a plant from its soil rhizosphere via the underground parts of the plant, and that inhibits biosynthesis of gibberellic acid(s) in the plant by inhibiting oxidation of kaurene to kaurenoic acid, the amount of said chemical being sufficient to delay the time of flowering of that genotype sufficiently to synchronize its flowering with the flowering of the later-flowering genotype.

2. A method according to claim 1 wherein the plant is a grass plant.

3. A method according to claim 2 wherein the plant is a cereal grain plant.

4. A method according to claim 3 wherein the plant is a wheat plant.

5. A method according to claim 1 wherein the chemical is paclobutrazol.

6. A method according to claim 5 wherein the plant is a grass plant.

7. A method according to claim 6 wherein the plant is cereal grain plant.

8. A method according to claim 7 wherein the plant is wheat.

9. A method for producing hybrid seed from two genotypes of a species of plant, which genotypes do not naturally flower at the same time after emergence from the soil, that method comprising providing in the soil in which the earlier-flowering candidate parent genotype is to be grown, or is growing, up to the stage of its development just prior to when anthesis begins, a chemical that is absorbed into the vascular system of a plant from its soil rhizosphere via the underground parts of the plant, and that inhibits biosynthesis of gibberellic acid(s) in the plant by inhibiting oxidation of kaurene to kaurenoic acid, the amount of said chemical being sufficient to cause that genotype or its progeny to flower at approximately the same time as the later-flowering candidate parent genotype flowers, thereafter causing cross-pollination between the two candidates, allowing the female candidate to develop until the seed is mature, and harvesting the seed.

10. A method according to claim 9 wherein the plant is a grass plant.

11. A method according to claim 10 wherein the plant is a cereal grain plant.

12. A method according to claim 11 wherein the plant is a wheat plant.

13. A method according to claim 9 wherein the chemical is paclobutrazol.

14. A method according to claim 13 wherein the plant is a grass plant.

15. A method according to claim 14 wherein the plant is a cereal grain plant.

16. A method according to claim 15 wherein the plant is wheat.

17. A method for producing A-line seed by fertilization of an A-line plant with pollen from a B-line plant that does not naturally flower at the same time after emergence from the soil as does the A-line plant, that method comprising providing in the soil in which the earlier-flowering candidate parent genotype is to be grown or is growing, up to the stage of its development just prior to when anthesis begins, a chemical that is absorbed into the vascular system of a plant from its soil rhizosphere via the underground parts of the plant, and that inhibits biosynthesis of gibberellic acid(s) by inhibiting the oxidation of kaurene to kaurenoic acid, the amount of said chemical being sufficient to cause that genotype or its progeny to flower at approximately the same time as the laterflowering candidate parent genotype flowers, thereafter causing cross-pollination between the two candidates, allowing the female candidate to develop until the seed is mature and harvesting the seed.

18. A method according to claim 17 wherein the plant is a grass plant.

19. A method according to claim 18 wherein the grass plant is a cereal grain plant.

20. A method according to claim 19 wherein the plant is a wheat plant.

21. A method according to claim 17 wherein the chemical is paclobutrazol.

22. A method according to claim 21 wherein the plant is a cereal grain plant.

23. A method according to claim 22 wherein the plant is wheat.

24. A method according to claim 1 wherein the effect of the chemical is modified by the later application of a gibberellic acid to control more precisely the time the treated plant flowers.

25. A method according to claim 1 wherein the chemical is N-(tert-butylcarbonyl)-N-(4'-chlorophenylmethyl)aminopyrazine.

26. A method according to claim 9 wherein the chemical is N-(tert-butylcarbonyl)-N-(4'-chlorophenylmethyl)aminopyrazine.

27. A method according to claim 17 wherein the chemical is N-(tert-butylcarbonyl)-N-(4'-chlorophenylmethyl)aminopyrazine.

* * * * *